United States Patent [19]
Pitesky

[11] Patent Number: 5,931,794
[45] Date of Patent: Aug. 3, 1999

[54] ALLERGY TESTING APPARATUS

[76] Inventor: Isadore Pitesky, 4001 Linden Ave., Long Beach, Calif. 90807

[21] Appl. No.: 08/955,370

[22] Filed: Oct. 21, 1997

[51] Int. Cl.$^6$ ........................................................ A16B 5/00
[52] U.S. Cl. ............................. 600/556; 604/46; 606/186
[58] Field of Search ............................. 600/556; 604/46, 604/47, 173; 606/186

[56] References Cited

U.S. PATENT DOCUMENTS

| | | | |
|---|---|---|---|
| 2,522,309 | 9/1950 | Simon | 128/2 |
| 3,289,670 | 12/1966 | Krug et al. | 128/2 |
| 3,512,520 | 5/1970 | Cowan | 600/556 |
| 3,688,764 | 9/1972 | Reed | 600/556 |
| 3,921,804 | 11/1975 | Tester . | |
| 4,222,392 | 9/1980 | Brennan | 604/47 |
| 4,237,906 | 12/1980 | Havstad et al. | 600/556 |
| 4,292,979 | 10/1981 | Inglefield, Jr. et al. | 600/556 |
| 4,304,241 | 12/1981 | Brennan | 600/556 |
| 4,453,926 | 6/1984 | Galy | 604/47 |
| 4,607,632 | 8/1986 | Brennan et al. | 600/556 |
| 4,714,621 | 12/1987 | Gullberg | 600/556 |
| 4,802,493 | 2/1989 | Maganias | 600/556 |
| 4,863,023 | 9/1989 | Payne et al | 600/556 |
| 5,154,181 | 10/1992 | Fishman | 600/556 |
| 5,417,683 | 5/1995 | Shiao | 604/173 |
| 5,538,134 | 7/1996 | Pitesky | 600/556 |
| 5,605,160 | 2/1997 | Fishman | 600/556 |
| 5,692,518 | 12/1997 | Baker et al. | 600/556 |
| 5,735,288 | 4/1998 | Fishman | 600/556 |
| 5,746,700 | 5/1998 | Hsiao | 600/556 |
| 5,749,836 | 5/1998 | Hsiao | 600/556 |

OTHER PUBLICATIONS

P. 23 of United Laboratory Plastics catalog on Screw Cap Micro Tubes, Jan. 1997.
Back cover of vol. 78, No. 6 of *Annals of Allergy, Asthma & Immunology* Multi–Test II and Duotip–Test, Jun. 1997.
*In re Lincoln Diagnostics, Inc.*, 30 USPQ2d 1817, Feb. 15, 1994.

*Primary Examiner*—Max Hindenburg
*Assistant Examiner*—Charles Marmor, II
*Attorney, Agent, or Firm*—Fulwider Patton Lee & Utecht, LLP

[57] ABSTRACT

An allergen testing pick for receipt in the open top end of a vial of allergen and including a neck for close fit with the top end of such vial. The pick includes a stem depending downwardly from such neck and is formed with a plurality of sharp tines. A device may be provided for receiving the vials and may be in the form of a plurality of individual modules releasably coupled together.

14 Claims, 4 Drawing Sheets

ALLERGY TESTING APPARATUS

BACKGROUND OF THE INVENTION

1. Field of the Invention

The present invention relates to a self loading and self sealing, disposable allergy testing apparatus.

2. Description of the Prior Art

Allergy testing involves subjecting a patient to a wide variety of different allergens to determine which allergens cause allergic reactions in the patient. Such testing requires that the respective allergens be applied beneath the surface of the patient's skin. There are two methods of intracutaneous allergen application, the first being the puncture method and the second abrasion. Ideally an allergen applicator should be capable of use in either the puncture or abrasion techniques, because skin thickness or toughness varies from patient to patient. The puncture method is accomplished by piercing the patient's skin with sharply pointed prongs while applying a drop of allergen. The second method, abrasion, involves abrading the skin through a drop of allergen using an abrading or scarifying device such as a sharp knife or chisel like instrument.

These abrading techniques can be satisfactorily performed only by technicians having considerable experience and sensitivity to the allergen used and the skin of the patient, as well as familiarity with the tool. Different technicians performing the same tests oftentimes do not achieve the same results because the intensity and penetration of the abrasion and amount of allergen introduced into the skin varies from patient to patient and is highly dependent on the particular manner in which the technique is carried out. The degree of variation is compounded by the fact that different patients possess different skin thickness and sensitivity.

The allergen, remaining in the vial, being expensive and sensitive to environmental exposure, should be conserved for subsequent application. Therefore, it is desirable that the allergen be stored in a container which can be easily sealed after use, and which will collect the residual allergen for effective use in subsequent applications. It is desirable that the pick be constructed to facilitate extraction of the residual allergen from the container and to subsequently seal the container without requiring inordinate manual dexterity or the use of extraneous tools. Since it is often desirable to vary the number of allergens tested on any particular patient, it would be preferable to be able to easily vary the number and type of allergen containers in a set to provide the technician the flexibility of varying the number of allergens in such set.

One device proposed for the delivery of allergen involves the use of a pick including a single, hollow cylindrical chisel to create capillary action when the chisel is submersed within the allergen. The hollow cylindrical bore is effective in allowing the device to hold the proper amount of allergen, and this device has been successfully used. However, this device is limited to delivering allergen to only one point within the patient's skin, limiting the amount of allergen which can be applied to the patient's skin. Also, because the device does not limit the depth of penetration of the chisel, dispensing the allergen to the proper depth within the patient's skin requires certain degree of skill on the part of the technician. This form of allergen applicator can be found in U.S. Pat. No. 4,304,241.

Another device proposed by the prior art is a single cylindrical stem formed at its bottom end with a bifurcated point to define a pair of blades. A device of this type has been marketed by Center Laboratories under the trademark DUOPICK-TEST®. Such devices suffer the shortcoming that they are awkward and inconvenient to handle and manipulate and are difficult to store. They fail to include any plug or support member or cover which might cooperate in holding the device erect, centered and sealed in a vial for convenient access. Moreover, with only two tines, the quantity of allergen which can be administered is limited.

One very commercially successful device, previously sold under the trademark DERMAPIK, incorporated an antigen assembly including a tray configured with upwardly opening wells dispersed thereabout and closed at their respective top ends by means of stoppers configured with a centrally disposed, severable bubble covering a small diameter entry passage. Thus, in practice, the technician could gain access to allergen stored in the vial by cutting off the bubble tip to create a small opening inserting a small diameter stem of an applicator through the small opening. A device of this type is shown in my U.S. Pat. No. 4,237,906. While having enjoyed great commercial success, such a device has the shortcoming that removal of the bubble cap is time consuming, requires some degree of dexterity and can contribute to contamination of the allergen. Additionally, the relatively close interfitting relationship between the stem and entry opening requires relatively steady nerves on behalf of the technician and some degree of patience for inserting the stem into the passage.

In this regard, the applicator stem shown in my U.S. Pat. No. 4,237,906 incorporates a circular array of relatively short, pyramidal shaped teeth for abrading the patient's skin. Such teeth were of relatively wide cross section at their base and throughout a major portion of their respective axial lengths thus rendering them unacceptable for applications where penetration was to be of any significant depth into the skin. Further, such teeth were not sized or arranged in such a manner as to provide for carrying of a sufficient quantity of allergen of the viscosity presently utilized in the medical field thus limiting its usage to technicians having some degree of experience and skill in performing the procedure.

A similar device has been used which employs a vial and a cap having a reduced in cross section opening. The cap is configured with a reduced in cross section opening and an upwardly extending collar. The collar is sized for receiving and being sealed by the handle of an applicator pick, which is installed within the cap and the stem of which extends into the vial. In use, this device eliminates the need to cut off a bubble top, being sealed by the handle of the applicator fitting within the cap, and therefore reduces the risk of contamination inherent in cutting of the bubble tip. However, as with the previous device, this device suffers the shortcoming of having an opening of relatively small diameter, making installation of an applicator pick difficult.

Several devices have been developed which apply a plurality of allergens simultaneously at predetermined spaced apart locations on the patient's skin. By applying all of the allergens simultaneously, these device are effective in reducing the duration of discomfort of the patient and have been successfully used in situations where the puncture technique has been the desired method of application. However, because allergen is being applied simultaneously at several adjacent locations, the device must be pressed straight down and often rocked back and forth onto the patient's skin, and the individual applicators cannot be twisted about their own axes as is required in the abrasion mode. A device of this type is especially problematic for use on patients having small diameter arms which do not provide a sufficiently flat surface for applying many allergens simultaneously. Devices of this type are shown in my U.S. Pat. No. 5,551,441 as well as in U.S. Pat. Nos. 2,522,309 and 5,154,181.

Still another device proposed includes a base having a set number of upwardly opening wells for receipt of individual picks covered collectively by a single removable cover or to be covered individually by separate well caps. While this device provides convenient access to and secure sealing of the allergen, it fails to provide the convenience and flexibility of providing a holder adapted to receive different sets of vials of allergen which can be changed to accommodate the differing needs of various patients. A device of this sort is shown in my U.S. Pat. No. 5,538,134.

Thus, there exists a need for an allergy testing device which is self sealing, self loading, and disposable with the proper quantity of allergen and which can be used for either a puncture application or abrasion application and with interchangeable vials.

SUMMARY OF THE INVENTION

Briefly, and in general terms, the present invention is directed to an allergy testing apparatus to significantly increase the ease with which the allergen can be accessed and stored. The apparatus includes an allergen applicator pick formed with a tip configured with a plurality of elongated thin abrading and/or puncture tines arranged to collectively hold a predetermined amount of allergen. Such pick can be formed with an integral plug for sealing an allergen vial, and has a handle which is ribbed or knurled to prevent slipping when used as an abrader. The apparatus, in some embodiments, includes interlocking trays, each having a selected number of vial receiving wells and selectively lockable together to form a tray assembly with various numbers of vial receiving wells.

In accordance with the invention, the allergy testing apparatus includes a tray having a plurality of downward extending cylindrical bores which hold a plurality of allergen vials preferably formed with wide mouth tops. The allergen vials are sealed at such tops by enlarged in diameter caps formed with the disposable allergen applicator picks to fit securely into such tops.

The rim of the vial is provided with a lip for resting on the top of the tray when the vial is inserted into the tray. The bottom of the vial may be rounded and formed with a central cylindrical sump into which the last few drops of allergen will collect. When the applicator pick is inserted into the vial, the tip of the applicator pick fits into the sump where the last few drops of allergen can adhere to the tip for easy removal, thereby assuring the effective use of all of the expensive allergen.

The applicator pick can be easily inserted into the relatively large mouth in the top of the allergen vial. When the allergen is to be used, the applicator pick is removed from the vial, and the allergen is applied to the patient. After use, the applicator pick is disposed of, and for the next patient a new sterile applicator pick may be inserted into the vial to seal the interior of the vial from outside contaminants until the next use of the allergen.

Advantageously, the applicator is provided with a plurality of sharply pointed conical tines at the bottom of its shaft. In use, the applicator pick is removed from the vial, thereby extracting a predetermined amount of allergen. The pointed tines are then used to either puncture or abrade the patient's skin, depositing the extracted allergen into the skin. The flat bottom of the shaft of the applicator pick from which the tines extend acts as a stop when the tines are puncturing the patient's skin, limiting penetration to a predetermined depth. In one embodiment, the center of the bottom of the applicator pick from which the tines project may be formed with a recess of a selected size to cooperate with the tines in holding a set amount of allergen.

In another particular aspect of the invention, two or more trays can be fastened together to provide an expandable test kit. A preferred method of fastening the trays together is by means of a male and female portion along opposite sides of the tray whereby one tray can be slip fit into another in tongue-and-groove fashion, however other fastening means may also be used.

In still another aspect of the invention a cap may be provided which fastens to the top of the vial by threaded or other fastening means.

In yet another possible aspect of the invention, the vial is provided with an extended finger grasp neck so that the vial may be easily withdrawn from the tray.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENT

In the following detailed description, like reference numerals will be used to refer to like or corresponding elements in the different figures of the drawings. Referring to the Figures, the allergy testing apparatus of the present invention is embodied in an apparatus 20 (FIG. 5) for testing a patient's reaction to one or more allergens by applying allergen under the skin of a patient. More particularly, the invention includes, generally, a set of applicator picks 22 (FIG. 2) for applying allergen under the skin of the patient, a set of vials 24, (FIG. 2) which contain allergen specimens and into which the applicator picks fit, and a tray 26, (FIG. 1) which holds the vials and applicator picks during testing and storage. Many novel features have been included in the design of the applicator pick, vial and tray which make use of the apparatus much more convenient and efficient. For example, the applicator pick has been provided with an integral enlarged in diameter plug 28 (FIG. 2) which fits into the open mouth 30 of the vial, thereby significantly reducing the number of parts required and allowing the vial to have a wider mouth opening for easy access. The applicator pick also includes improved long conical tines 32 (FIG. 9) at its bottom which facilitate skin puncture and provide effective application of allergen. The applicator pick is versatilely designed to be used in either the puncture or abrasion modes. The vial, being sealed at the top by the plug of the applicator pick, has a wide mouth opening for easy insertion of the applicator pick, and is provided at its bottom with a sump 34, referred to in FIG. 7, which ensures efficient use of substantially all of the expensive allergen. The tray into which the vials and applicator picks are held is configured such that two or more trays can be attached together, providing significantly enhanced flexibility and convenience to the technician at nominal cost, and is further provided with a clear plastic cover making storage more convenient.

Figures 7, 8:
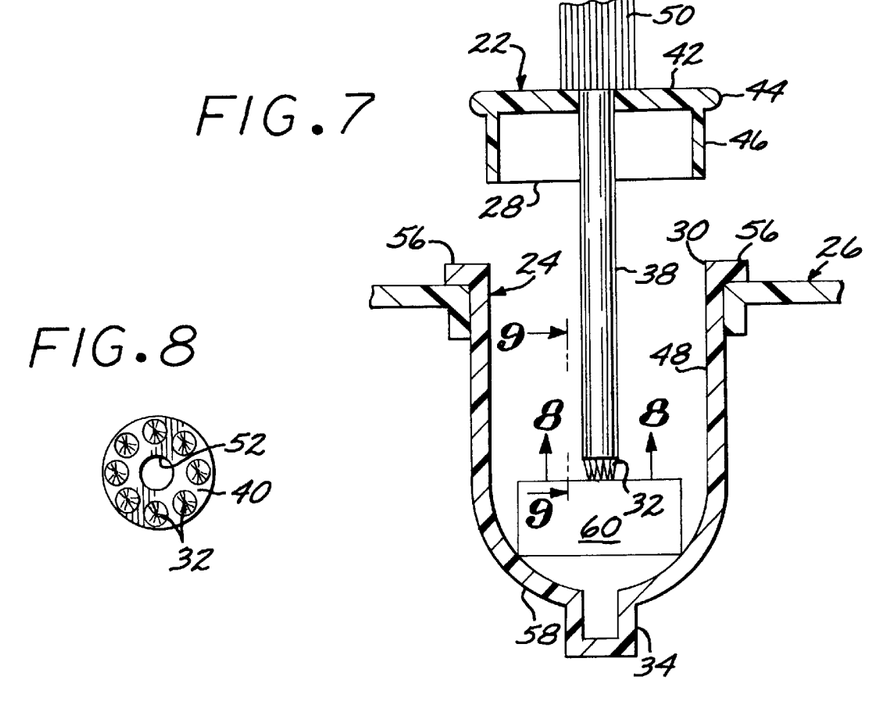
FIG. 7 is a transverse sectional view, in enlarged scale, taken along line 7—7 of FIG. 5 showing the applicator being inserted into the vial while the vial is installed in the tray.
FIG. 8 is an end view, in enlarged scale, taken along line 8—8 of FIG. 7.

The picks are configured centrally with cup shaped plugs 28 for removable receipt in the respective vial mouths 30 having downwardly depending narrow stems 38 about 4 millimeters in diameter. Such stems are formed at their bottom extremities with a circular pattern of downwardly depending sharp, conical, pointed tines 32 (FIG. 7). The tines serve primarily two functions. First, they provide a capillary action by increasing the surface area at the bottom of the stem, thereby allowing the desired amount of allergen to adhere to the bottom of the applicator pick. This ensures that a proper dosage of allergen will be administered to the patient during any given application. Secondly, the tines are used to apply the allergen into the skin of the patient. Because they are of a selected length and sharply pointed, the tines can pierce the skin of the patient, thereby allowing the predetermined quantity of allergen suspended from the tip of the applicator pick to be deposited into the patient's skin for effective reaction in the patient.

The relatively long conical shape of the tines 32 (FIG. 9) is optimum for use in either the puncture or abrasion modes. This is because the conical shape provides a sharp point while minimizing the surface area of the tine. By minimizing the cross section of the tines, providing a circular shape and a selected length, the resistance to penetration of the tine by the patient's skin is reduced. The conical shape of the tip of the tines also provides symmetrical structural rigidity about the entire radius of the tine, thereby uniformly resisting bending loads in any direction. The conical shape further provides a diameter which increases linearly down the length of the conical tip. When the applicator pick is used in the abrasion mode, a force is exerted near the tip of the tine perpendicular with longitudinal axis of the tine. This force causes a bending stress in the tine which increases linearly with distance from the tip of the tine. Having a diameter which increases linearly down the length of the tine causes the tine to have a stiffness which is directly proportional to the linearly increasing bending stress along the length of the tine. The tines terminate at the flat bottom wall 40 of the stem 38 (FIGS. 8 and 9), creating a stop to limit penetration of the tines. In this way each of the tines can easily be inserted into the patient's skin to a precise, predetermined depth.

Referring to FIG. 7, at the top of the narrow stem 38 of the applicator pick 22, and integral therewith, is formed a downwardly opening cup shaped plug 28 which is configured with an outer periphery to fit snugly into the top of the allergen vial 24, securely sealing the allergen therein. The plug 28 consists of a circular horizontal disk 42 radially and concentrically disposed about the longitudinal axis of the shaft 38 and configured with a parametrial annular lip 44. Extending downward from the outer edge of the disk is a cylindrical sleeve 46. The sleeve is configured for free and sliding fit within the collar 48 defining the mouth of the vial 24. By constructing the cap integral with the applicator pick, greater efficiency is achieved. Projecting above the cup shaped plug 28, is an upstanding handle 50 referred to in FIG. 2. The handle is knurled or ribbed to allow easy gripping by the technician, and is of sufficient diameter to make the applicator pick easy to manipulate.

With reference to FIG. 7, the lip 44 projects radially outwardly about the entire perimeter of the plug 28 to define a limit ring projecting radially outwardly beyond the cylindrical sleeve 48. When the applicator pick and its cap are fully inserted into the vial 24, the lip 44 nests on the top edge of the vial. In this way, the lip of the plug 28 acts as a stop, allowing the applicator to be easily and consistently inserted the proper distance into the vial 24. By causing the applicator pick 22 to be inserted the proper distance into the vial, the tip of the applicator will be correctly placed in the bottom of the vial in a location which is optimal for collecting allergen but in which the tip will not contact the bottom of the vial.

Figures 9, 10:
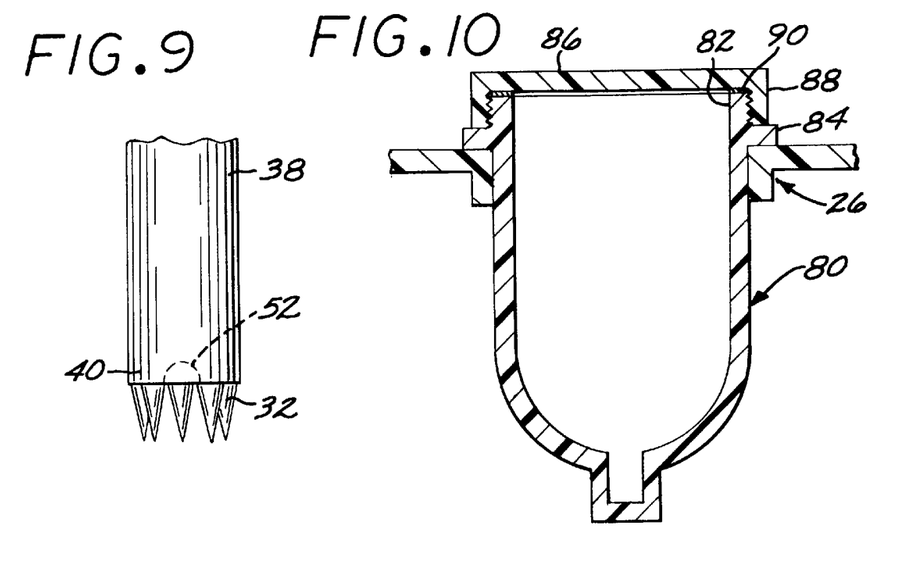
FIG. 9 is a side view, in enlarged scale, taken along line 9—9 of FIG. 7.
FIG. 10 is a sectional view similar to FIG. 7 but showing an optional vial with a threaded cap on the open mouth.

In the preferred embodiment referred to in FIGS. 8 and 9, the applicator pick 22 can include from six to eight conical tines 32 but preferably includes eight tines 32 arranged in a circular pattern about the bottom of the applicator pick. In the center of the circular pattern, a downwardly opening semi-spherical allergen cup 52, referred to in FIG. 8, is formed in the bottom wall 40 of the stem 38. The tines cooperate to provide a capillary action causing allergen to adhere to the tip of the applicator pick 22, and the cup 52 further increases the capillary action. The tines 32 can be arranged in different patterns but in the preferred embodiment are disposed in a circular pattern about the central axis of the pick 22 in a pattern defining a circle 3 mm. The individual tines may be of various lengths such as from 0.5–2 mm, but are preferably about 0.2 mm in diameter at their respective bases and 1 mm long. Likewise, the cup, 52 which can be of various depths, is preferably configured with a radius of 0.1 mm to provide a corresponding depth.

Figures 1, 2:
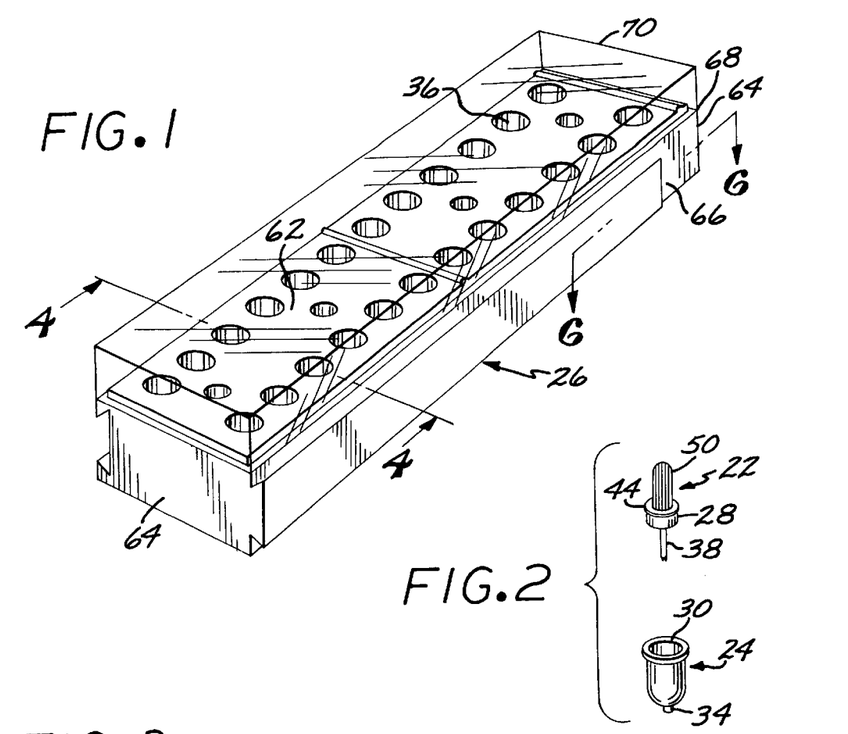
FIG. 1 is a perspective view of a tray apparatus for holding allergen vials of the allergy testing apparatus of the present invention.
FIG. 2 is a perspective view of an allergen vial and applicator pick of the present invention.

Referring to FIG. 2, the vial 24 is cylindrically shaped and designed to fit within one of several wells 36 which are provided in a tray 26 as referred to in FIG. 1. With reference to FIG. 7, the vial is formed with the upwardly opening collar 48 into which the sleeve 46 of the plug 28 of the applicator pick 22 tightly fits, and has a generally curved, closed bottom. Extending radially outwardly from the top edge of the collar is a lip 56 which nests upon the top surface of the tray to act as a stop to support the vial. The collar 48 forms a large interior diameter defining a mouth 30 of 1.0 centimeters to facilitate ease of insertion of the applicator pick. The stem 38 of the applicator pick 22, having a much smaller cross section than the large opening of the vial, can be easily inserted into the vial without requiring a high degree of manual dexterity on the part of the technician.

With continued reference to FIG. 7, the curved bowl shaped bottom wall of the vial 24 is provided with a downwardly depending small cylindrical sump 34, configured for complemental receipt of the bottom end of the pick 22 and into which the allergen collects. When the applicator pick 22 is fully inserted into the vial, the tip of the applicator will be disposed within the sump, thereby allowing allergen contained within the sump to adhere to the tip of the applicator. Use of the sump assures that substantially all of the expensive allergen will be effectively used and further assures that the last application from the vial will deliver the proper amount of allergen for delivery to the patient.

Referring again to FIG. 7, the exterior wall of the vial is provided with a frosted patch 60 of roughened texture which can be written on using a standard marker. This allows the technician to easily label the vial, further increasing convenience to the technician.

The tray 26, referred to in FIGS. 1, 3, 4 and 5, is generally in the form of a block shaped, open bottom plastic shell having a flat rectangular top wall 62, opposite end walls 64 and elongated side walls 66. Formed integral with the top wall are a plurality of, upwardly opening cylindrical wells 36 for receiving the vials 24 of allergen. It has been found that a set of 24 wells 36 arranged in two rows of twelve each provides for holding a sufficient number of vials for many applications. The wells extend only slightly downward from the top of the tray 26. It will be appreciated that in the event it becomes necessary to change a vial 24 it can be easily pushed up from beneath to dislodge the vial. The tray is formed about its upper periphery with an outwardly and upwardly opening perimetrical notch 68 (FIGS. 1, 4 and 5) for complemental receipt of the lower edge of a box-like transparent, downwardly opening lid, generally designated 70. The tray and lid combine to provide, even with the wells filled with vials, the overall combination with a brick like shape so such vial filled trays and lids may be easily stacked for storage and shipping. The trays can also be stacked and immobilized without the lid.

Figure 3:
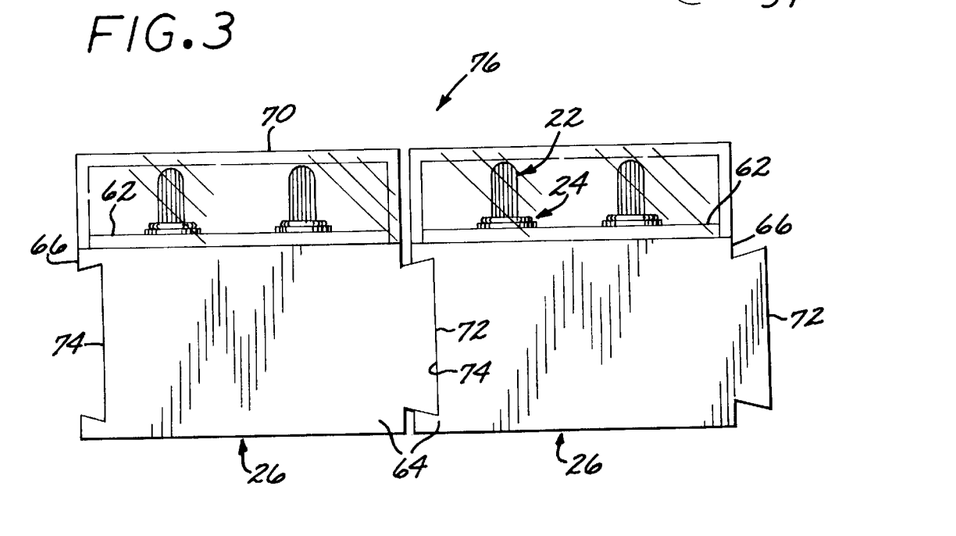
FIG. 3 is a left end view, in enlarged scale, of a pair of tray apparatus as shown in FIG. 1, assembled together showing the pick of FIG. 2, in enlarged scale.
Figure 4:
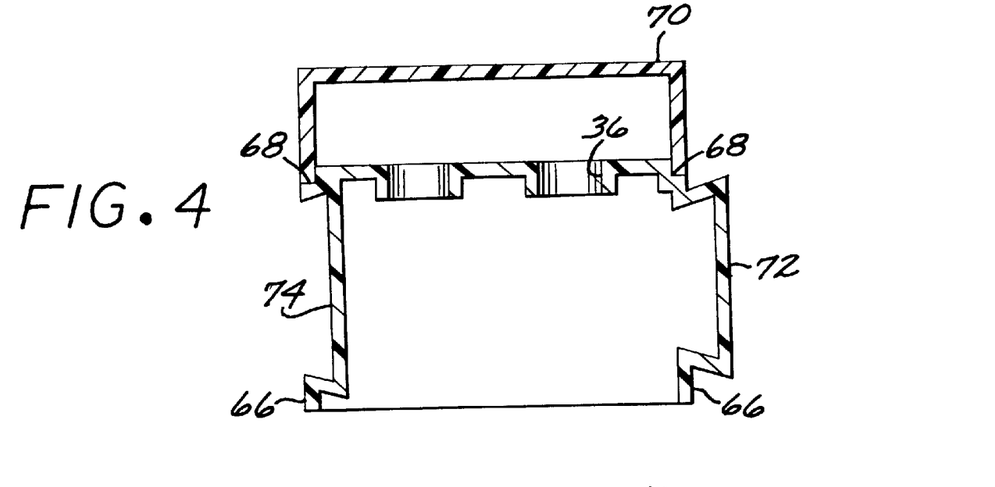
FIG. 4 is a transverse sectional view, in enlarged scale, taken along line 4—4 of FIG. 1.
Figure 6:
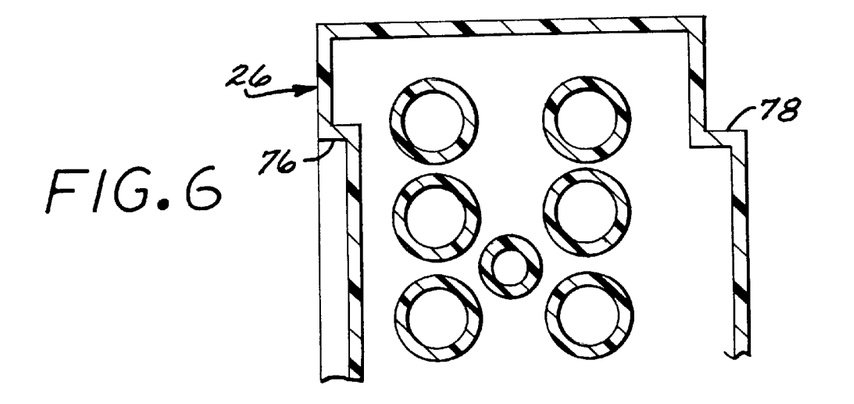
FIG. 6 is a sectional plan view, in enlarged scale, taken along line 6—6 of FIG. 1

The tray 26 is formed in its opposite side with a respective longitudinal tongue 72 and grooves 74 to facilitate attaching two or more trays together to form a larger kit, generally designated 76, shown in FIG. 3. The tongue and groove are formed with a dovetail cross section for sliding interlocking relationship. Referred to in FIG. 6, the grooves 74 are open on one end of the tray but stop short of the other end, thereby providing a groove end 76 to be engaged by a stop 78 formed at one end of the tongue 72 a short distance from the corresponding end wall of such tray, to limit sliding of such connecting tongue rail to maintain such trays aligned in flanking relationship. In this way, the technician can slide two trays together until the stop 78 of one tray reaches the groove end 76 in the second tray at which point the two trays will be perfectly adjacent and securely attached to one another. The capability of connecting two or more trays together is an important advantage to the technician. If a patient requires use of only a small number of allergens, then the single tray can be used. However, if a patient requires testing of a greater number of allergens, the kit can be expanded to include all of the required allergens in one convenient kit for rapid and efficient use to apply all the allergen prescribed for the particular patient.

It will be appreciated by those skilled in the art that the trays 26 and lid 70 (FIG. 1) can be conveniently and inexpensively constructed of thermoplastic material. Likewise, the vial 24 and applicator pick 22 can be molded of thermoplastic using an injection molding process.

Figure 5:
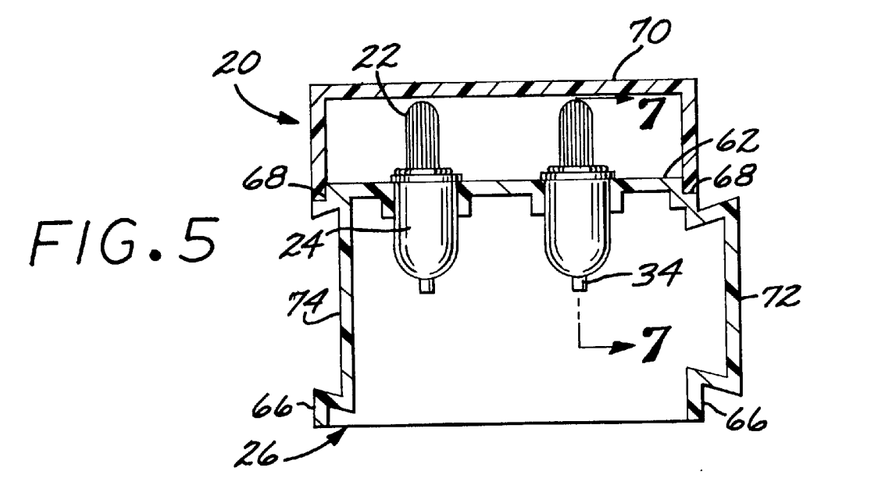
FIG. 5 is a transverse sectional similar to FIG. 4 showing a pair of applicators inserted, view taken along line 5—5 of FIG. 1.

In operation, the trays 26, vials 24, applicators 22 and lid 70, referred to in FIG. 5, may be shipped from the factory to the office of the doctor or laboratory technician. When a patient is to be treated with, for instance, approximately 24 or less allergens, only a single tray may need be used. When a patient is to be tested for allergenic reaction, the allergenic extracts or allergens to be tested on the patient may be selected. Vials 24 containing those allergens may be inserted in the respective wells of the tray and filled with the selected allergen. To facilitate identification of the vials of allergen, the operator may label the allergen vials by writing an identification or code on the frosted patch 60 of each of the selected vials using a pen or other standard writing implement.

In the event the technician elects to apply a number of allergens greater than that for the number of wells in a particular tray 26, it is convenient to merely couple two or more trays together, as shown in FIG. 3, to provide the desired number of vials carried in the various wells 36. In this fashion, assuming the technician sought to administer, for instance 38 different allergens, two trays would be coupled together by sliding the tongue 72 of one tray into the open end of the dovetail groove 74 of the adjacent tray to the extent permitted by groove end 76 and stop 78 (FIG. 6) thus assuring longitudinal alignment of the respective trays to provide a pair of modules having a total capacity of, for instance, 44 vials. Assuming the technician proceeds with the 38 different vials selected, the wells of one full tray 26 may be filled with respective vials, and 16 wells of the second tray may likewise be filled with vials. The vials will be typically prefilled with allergen before the procedure is commenced so that the technician can quickly and efficiently remove the picks from the respective vials 24 and administer the allergen as described hereinabove to thereby provide for treating the patient in the minimum amount of time and thus minimize the period of time to which the patent is subject to the trauma and stress associated with any concern which may be raised about the overall procedure.

As the technician then treats the patient, the picks 22 (FIG. 3) may be withdrawn in progression from the respective vials 24. As the respective stems 38 (FIG. 2) are withdrawn from the allergens in the respective vials, the capillary action of the allergens will cause a selected quantity of such allergens to adhere to the surfaces of the respective tines 32 (FIG. 9) and bottom wall 40 of the stem 38 and within the confines of the allergen cup 52 (FIGS. 8 and 9). in this regard, it will be apparent to those skilled in the art that allergens have generally the same viscosity and, within reason, the same general capillary characteristics, such that the desired quantity of allergen will remain adhered to the tip of the stem as it is removed from the vial. The technician may then apply the allergen beneath the patient's skin by, pressing the end of the applicator pick against the patients skin using either the puncture or abrasion techniques.

It will be appreciated that this option of utilizing the individual pick for administration of the allergen by either a puncture method or an abrading or scarifying method is of great advantage. Referring to FIGS. 7, 8, and 9, for the puncture method the technician will merely move the pick 22 over the skin with the residual allergen fluid adhered by capillary action to the surfaces of the tines 32, bottom wall 40 and cup 52. The technician may then press the stem inwardly to cause the points of such tines to puncture the skin to the full depth dictated by the length of such tines thus forming tiny puncture holes arranged in a circular pattern to introduce the quantity of allergen held thereon. Since the quantity of allergen and maximum depth of the puncture is already predetermined, the depth of penetration and amount of allergen introduced is limited. Consequently, this administration can be performed by a technician with a minimal amount of experience and understanding of the medical ramifications thereof.

If the particular technician or procedure undertaken is perceived to achieve better results by what is known as the "scratch test" where the skin is typically abraded by a scarifying device, the applicator of the present invention can be utilized by even the most inexperienced technician. In this approach, when the points of the tines 32 (FIG. 9) initially penetrate the skin, the technician may twist the handle 50 (FIG. 2) to rotate such stem about its longitudinal axis causing the points to scratch the skin surface often in a circular pattern, making small cuts therein for positive introduction of the allergen carried on such tines. It will thus be apparent to those skilled in the art that it is important that the pick incorporate a number of thin tines 32 to thus project from a stop a distance sufficient to reach under the skin to distribute the desired quantity of antigen in a puncture test and that such tips be sufficiently fine to provide for cutting of fine scratches in a scratch test when the pick is merely twisted about the longitudinal axis of the stem.

The used pick 22 referred to in FIG. 2 will then be discarded and, if desirable, a new pick selected for each of the vials of the tray and inserted into the vial at the end of the test to act as a stopper to maintain the biological cleanliness of the allergen until the next application for the subject patient or subsequent patient. It will be appreciated that the applicators may be easily inserted in the wide mouth 30 of the vials by inserting the respective stems 38 which, as the applicator is lowered into the vial as shown in FIG. 7, act to maintain the pick somewhat centered in the vial to thus lead the pick therein, as it is lowered, to thereby tend to register the skirt 46 of the plug 28 concentrically with the mouth 30 so that the technician may quickly and positively register such plug into sealing position for positive sealing thereof. The procedure will then be repeated for each of the picks in the vials positioned in the tray 26 (FIG. 5). When all of the picks have been discarded, the technician will know that this particular treatment of the patient has been completed.

Before the tray is stored, the technician may proceed to insert new sterile picks 22 (FIG. 2) into the respective vials 24 so that the respective mouths 30 of the vials will be closed by the respective plugs 28 of the new picks 22 or covered by the lid. It will be appreciated that insertion of the picks will be considerably easier due to the much larger diameter, wide mouth 30 cylindrical top opening of the vial. For storage, the clear plastic cover 70 (FIG. 5) may be placed onto the tray to further protect the allergens therein, and to allow the assembled allergy testing kits 20 to be easily stacked, significantly saving storage space.

In an alternate embodiment, shown in FIG. 10, a vial 80 is provided, substantially the same as the vial referred to in FIGS. 1–7 but including a rim or skirt 82 projecting upwardly above the lip 84 and threaded on its exterior for engagement with the cylindrical wall of a closure cap, generally designated 86. The cap is conveniently constructed of plastic and formed with a cylindrical stub wall 88 formed on its interior with mating threads. An annular compression seal 90 may be frictionally held within the cap 86 for sealing against the annular top edge of the vial 80.

In operation, it will be appreciated that the vial 80 of FIG. 10 may be loaded with an allergen and the cap 86 screwed thereonto in tight sealing relationship so that the presterilized vial may be maneuvered about, stored, or shipped with its allergen contained therein and the cap in place. When the technician is then to gain access to the vial for utilizing the allergen, the cap 86 may be unscrewed and discarded. The pick 22 (FIG. 7) may then be inserted in place to move the plug 28 into sealing relationship with the mouth of the vial.

Figure 11:
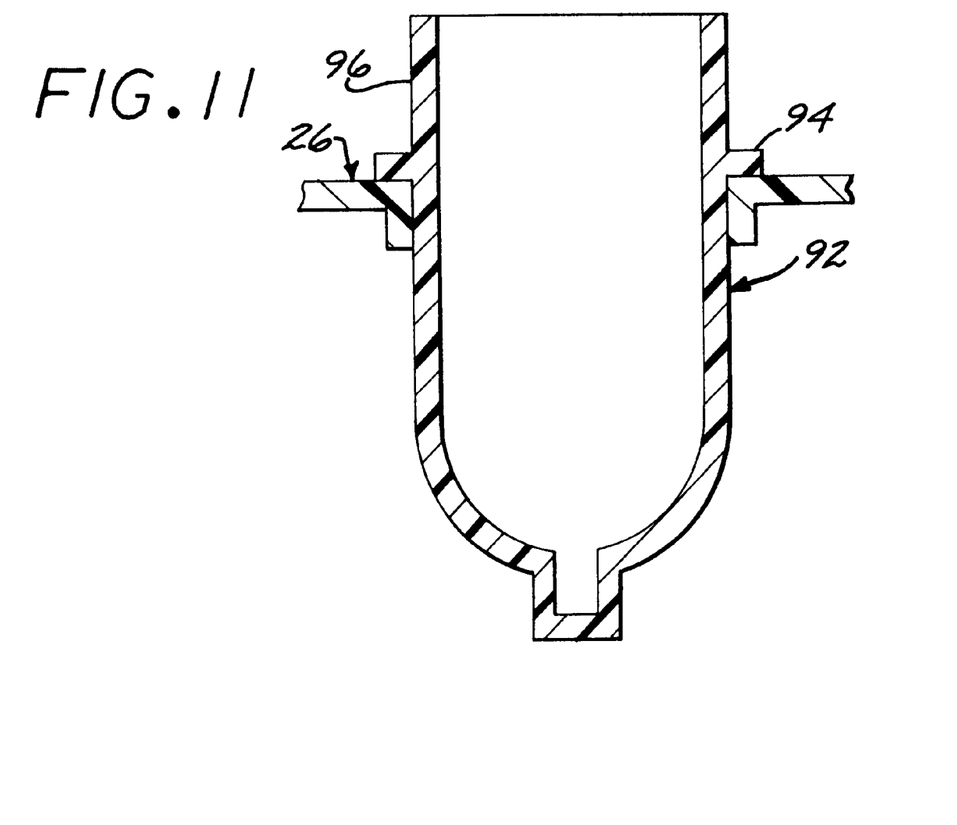
FIG. 11 is a sectional view similar to FIG. 7 but showing a third embodiment of the vial.
Figure 12:
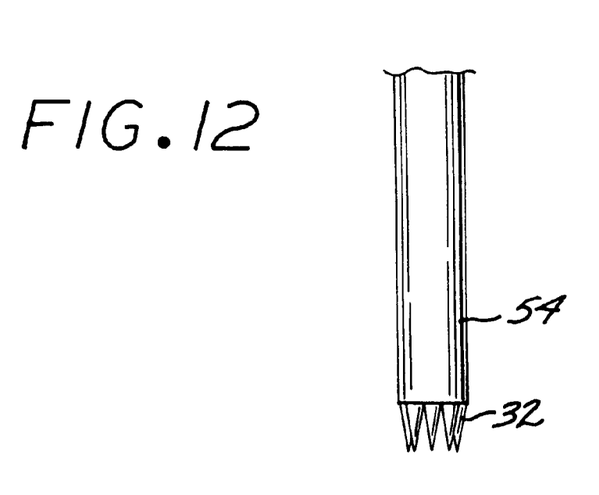

In another alternate embodiment, referred to in FIG. 11, a vial, 92 is provided which is similar to the vial 24 referred to in FIGS. 1–7 except that it projects vertically above a nesting lip 94 to define a cylindrical hand grasp rim 96.

In use, this embodiment allows convenient removal and interchange of vials 92 within a tray 26 referred to in broken sectional view in FIG. 11. If the technician desires to change the vials in a tray to accommodate the needs of a patient, the vial can be easily removed by grasping the rim 96 between the technician's thumb and index finger. This embodiment obviates the need to force the vial up from beneath, greatly increasing convenience to the technician.

From the forgoing it will be appreciated that the invention provides significant cost savings while including features which greatly enhance convenience and versatility. The disclosed use and arrangement of conical tines and use of a central bore will create the most effective and versatile applicator pick. It will also be clearly evident that the use of a cap integral with an applicator pick provides added economy and convenience by significantly reducing the number of parts required as well as by allowing the applicator pick to be inserted into the relatively large opening in the top of the vial. Convenience is also achieved by obviating the use of a knife or other tool to open the vial. It will also be appreciated that the invention provides greater flexibility by allowing a large number of allergens to be included in one kit by fastening several trays together. Finally, providing a clear cover for the tray makes storage more convenient. While several particular forms of the invention have been illustrated and described, it will also be apparent that various modifications can be made without departing from the spirit and scope of the invention.

What is claimed is:

1. An antigen pick device for selectively puncturing or abrading the skin of a patient to apply a selected antigen and comprising:
   an upstanding handle;
   a plastic shaft depending from said handle formed with a downwardly depending stem having a longitudinal axis and terminating in a bottom end; and
   a plurality of elongated thin plastic solid tines projecting downwardly a distance greater than 0.5 mm from said bottom end and terminating in respective puncture points to puncture through the skin of a human patient, said tines being so configured and sized as to be utilized to selectively abrade or puncture said skin to apply said selected antigen thereto whereby a medical technician may grasp said handle applying antigen to said tines and proceed endeavoring to puncture a patient's skin to a depth greater than 0.5 mm or, and the technician, may engage said points with the patient's skin and rotate said stem about said axis to cut the surface of such skin.

2. The device of claim 1, wherein:
said handle and stem are cylindrically shaped.

3. The device of claim 1, wherein:
said stem is tapered along the length thereof.

4. The device of claim 1, wherein:
said tines are conical.

5. The device of claim 1, wherein:
said bottom end of said antigen pick is formed with a centrally disposed, downwardly opening measuring reservoir.

6. The device of claim 1 for use in applying a predetermined liquid antigen, and wherein:
said tines are sufficient in number and so arranged as to, when withdrawn from immersion in a bath of said antigen in a vial, suspend a selected quantity of said antigen therebetween.

7. The device of claim 1, wherein:

said points are sharp.

8. The device of claim 1, wherein:

said tines are arranged in a circular pattern.

9. The device of claim 1, wherein:

said tines are of a length no greater than 2 millimeters.

10. The device of claim 1, wherein:

said tines are 1 millimeter long.

11. The device of claim 1, wherein:

the number of said tines ranges from 6 to 10.

12. The device of claim 1, that includes:

8 said tines.

13. The device of claim 1, wherein:

said pick is constructed of a polymer.

14. An antigen applicator device comprising:

an upright vial formed with a cylindrical side wall having a constant diameter throughout and terminating at its upper extremity in a mouth of said diameter;

a plastic pick including an upstanding handle and downwardly depending, reduced-in-cross section, stem terminating in a bottom end;

a plug formed with said stem and having an outside diameter formed to be received slidably in said mouth; and a plurality of elongated thin tines projecting downwardly from said bottom end a distance greater than 0.5 mm and formed with respective puncture points for puncturing through the skin of a human patient, said tines being so configured and sized as to be utilized to selectively abrade or puncture said skin to apply said selected antigen thereto.

\* \* \* \* \*